United States Patent [19]
DeFonzo et al.

[11] Patent Number: 5,782,753
[45] Date of Patent: Jul. 21, 1998

[54] SURGICAL RETRACTOR

[75] Inventors: Stephan A. DeFonzo, Bridgeport; David M. Farascioni, Danbury; Corbett W. Stone, Newtown, all of Conn.

[73] Assignee: United States Surgical Corporation, Norwalk, Conn.

[21] Appl. No.: 546,008

[22] Filed: Oct. 20, 1995

[51] Int. Cl.⁶ ...................................................... A61B 11/02
[52] U.S. Cl. ........................ 600/210; 600/201; 600/214; 600/215; 600/235
[58] Field of Search ...................................... 600/201, 210, 600/213, 214, 215, 226, 231, 235

[56] References Cited

U.S. PATENT DOCUMENTS

| | | |
|---|---|---|
| Re. 34,150 | 12/1992 | Santilli et al. . |
| 2,383,705 | 8/1945 | Bortagaray . |
| 2,473,266 | 6/1949 | Wexler . |
| 2,693,795 | 11/1954 | Grieshaber ............ 600/213 |
| 2,751,902 | 6/1956 | Loeffler . |
| 3,070,088 | 12/1962 | Brahos . |
| 3,227,156 | 1/1966 | Gauthier . |
| 3,384,078 | 5/1968 | Gauthier . |
| 3,467,079 | 9/1969 | James . |
| 3,509,873 | 5/1970 | Karlin et al. . |
| 3,522,799 | 8/1970 | Gauthier . |
| 3,680,546 | 8/1972 | Asrican . |
| 3,724,449 | 4/1973 | Gauthier . |
| 3,747,592 | 7/1973 | Santos . |
| 3,749,088 | 7/1973 | Kohlmann . |
| 3,965,890 | 6/1976 | Gauthier . |
| 4,010,741 | 3/1977 | Gauthier . |
| 4,156,424 | 5/1979 | Burgin . |
| 4,165,746 | 8/1979 | Burgin . |
| 4,263,899 | 4/1981 | Burgin . |
| 4,421,107 | 12/1983 | Estes et al. . |
| 4,566,448 | 1/1986 | Rohr, Jr. . |
| 4,616,635 | 10/1986 | Caspar et al. . |
| 4,622,955 | 11/1986 | Fakhrai . |
| 4,627,421 | 12/1986 | Symbas et al. . |
| 4,726,356 | 2/1988 | Santilli et al. . |
| 4,747,394 | 5/1988 | Watanabe . |
| 4,747,395 | 5/1988 | Brief . |
| 4,754,746 | 7/1988 | Cox . |
| 4,765,311 | 8/1988 | Kulik et al. . |
| 4,793,346 | 12/1988 | Mindich . |
| 4,813,401 | 3/1989 | Grieshaber . |
| 4,829,985 | 5/1989 | Couetil . |
| 4,852,552 | 8/1989 | Chaux . |
| 4,865,019 | 9/1989 | Phillips . |
| 4,924,857 | 5/1990 | Mahmoodian . |
| 4,949,707 | 8/1990 | LeVahn et al. . |
| 5,025,779 | 6/1991 | Bugge . |
| 5,052,373 | 10/1991 | Michelson . |
| 5,052,374 | 10/1991 | Alvarez-Jacinto . |
| 5,067,477 | 11/1991 | Santangelo . |
| 5,231,974 | 8/1993 | Giglio et al. . |
| 5,299,563 | 4/1994 | Seton . |
| 5,373,840 | 12/1994 | Knighton . |
| 5,400,774 | 3/1995 | Villalta et al. . |

FOREIGN PATENT DOCUMENTS

| | | |
|---|---|---|
| 2302078 | 9/1976 | Germany . |
| 116547 | 6/1918 | United Kingdom . |
| 2082459 | 8/1981 | United Kingdom . |

*Primary Examiner*—Beverly M. Flanagan

[57] ABSTRACT

A surgical retractor comprising a base adapted to lie on the patient's skin, a handle slidably mounted with respect to the base, a tissue retracting blade extending from the handle, and a locking member movable from at least a first position to a second position to retain the tissue retracting blade in a selected position. A method for accessing the saphenous vein to facilitate harvesting the vein is also disclosed comprising the steps of making a small incision in the leg of a patient, positioning a retractor on a patient's leg such that a retractor blade extends into the incision and a base lies on the surface of the patient's leg and pulling the retractor blade away from the patient to lift the tissue away from the underlying saphenous vein.

24 Claims, 8 Drawing Sheets

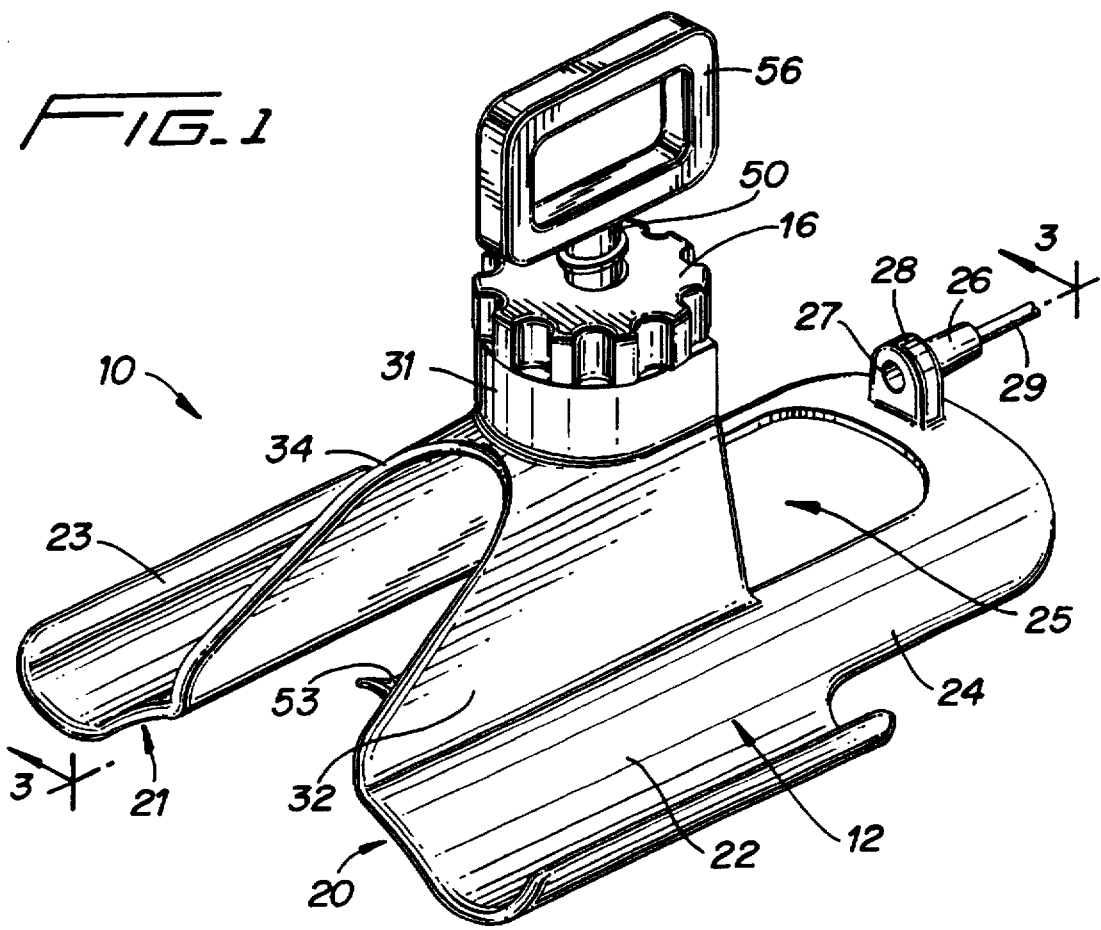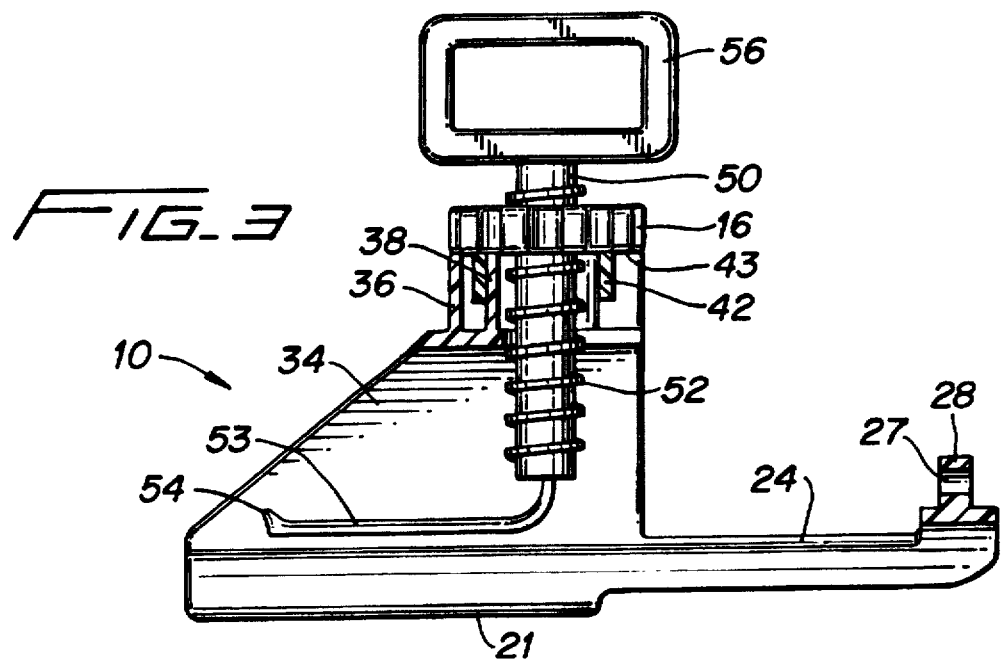

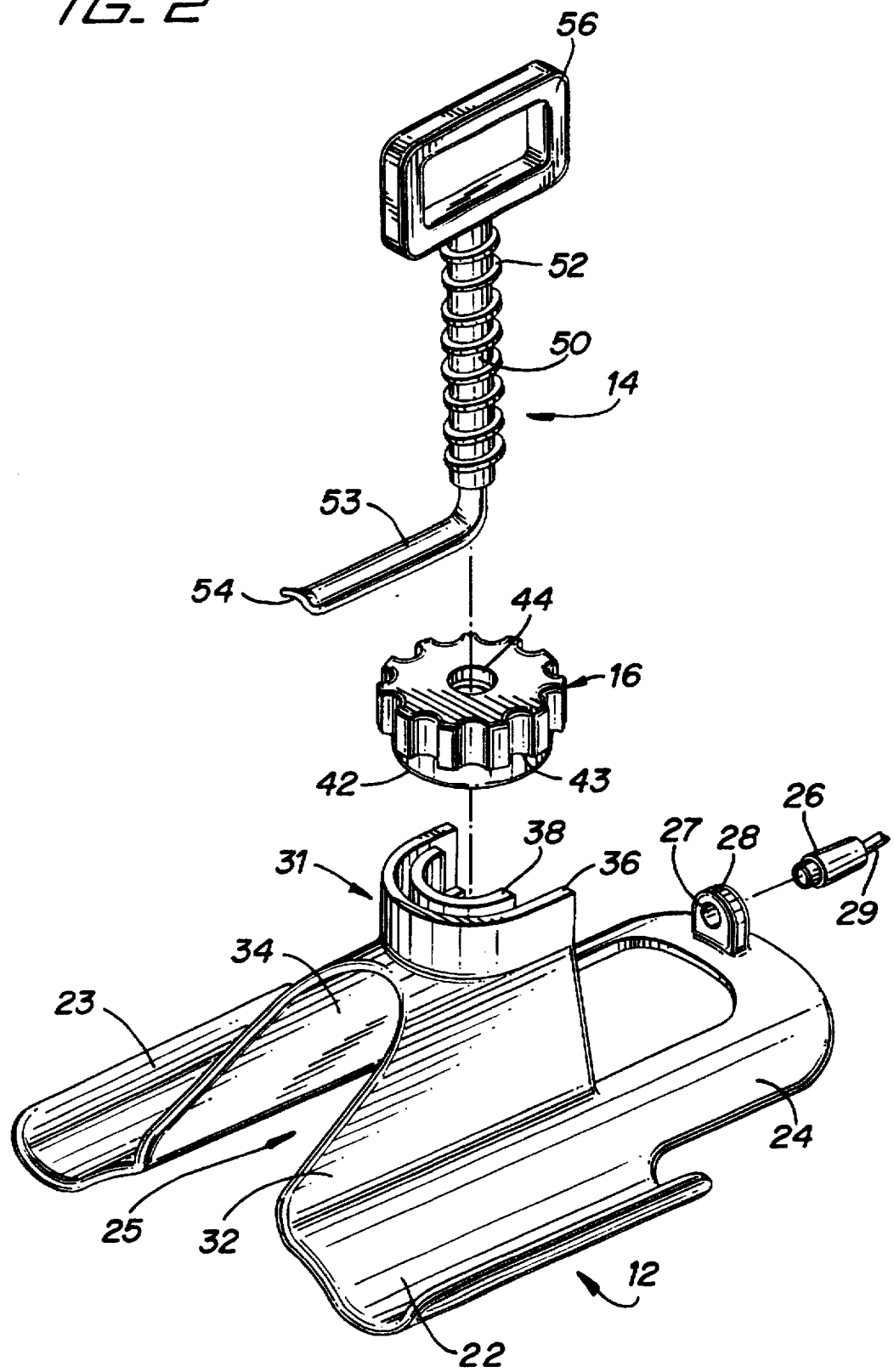

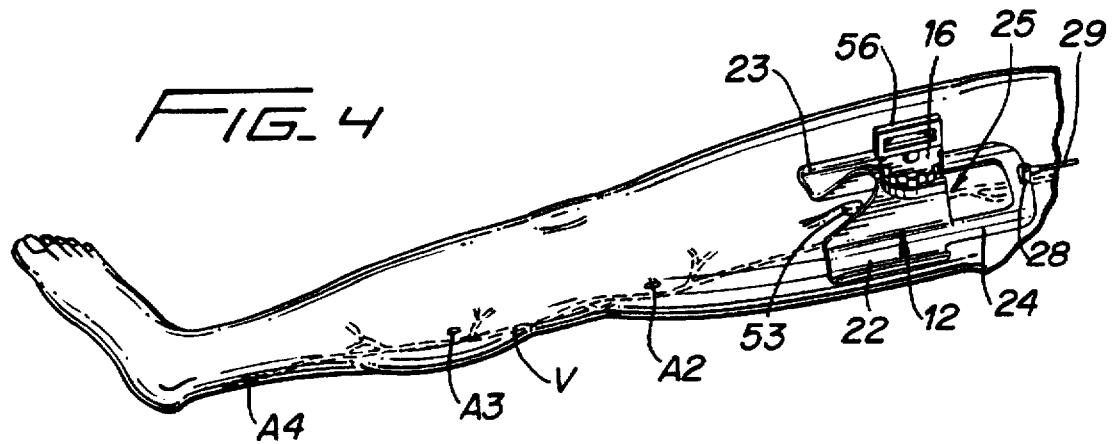
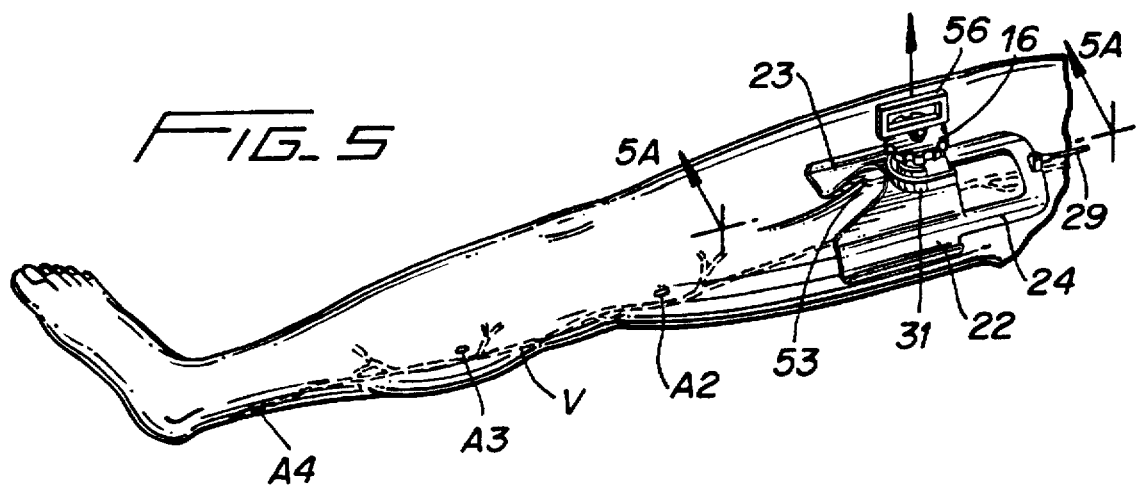
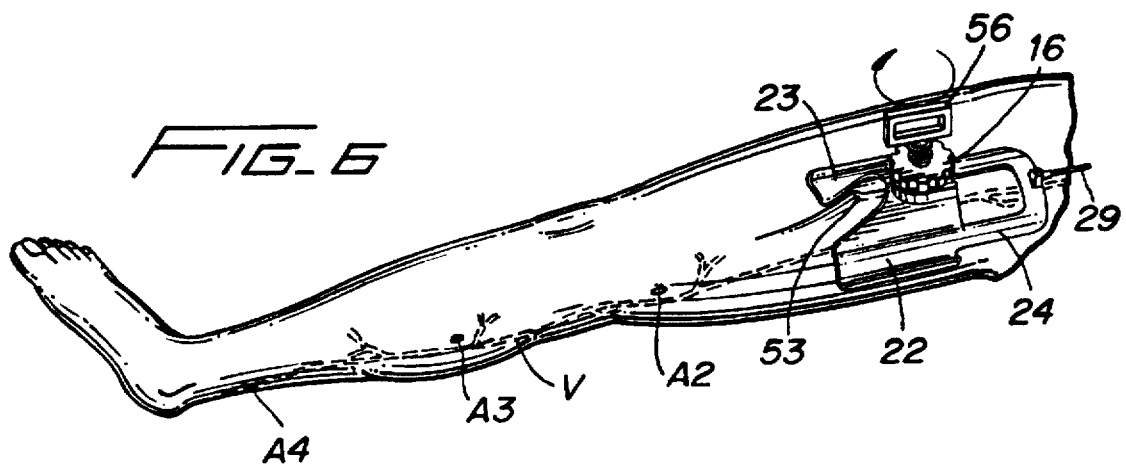

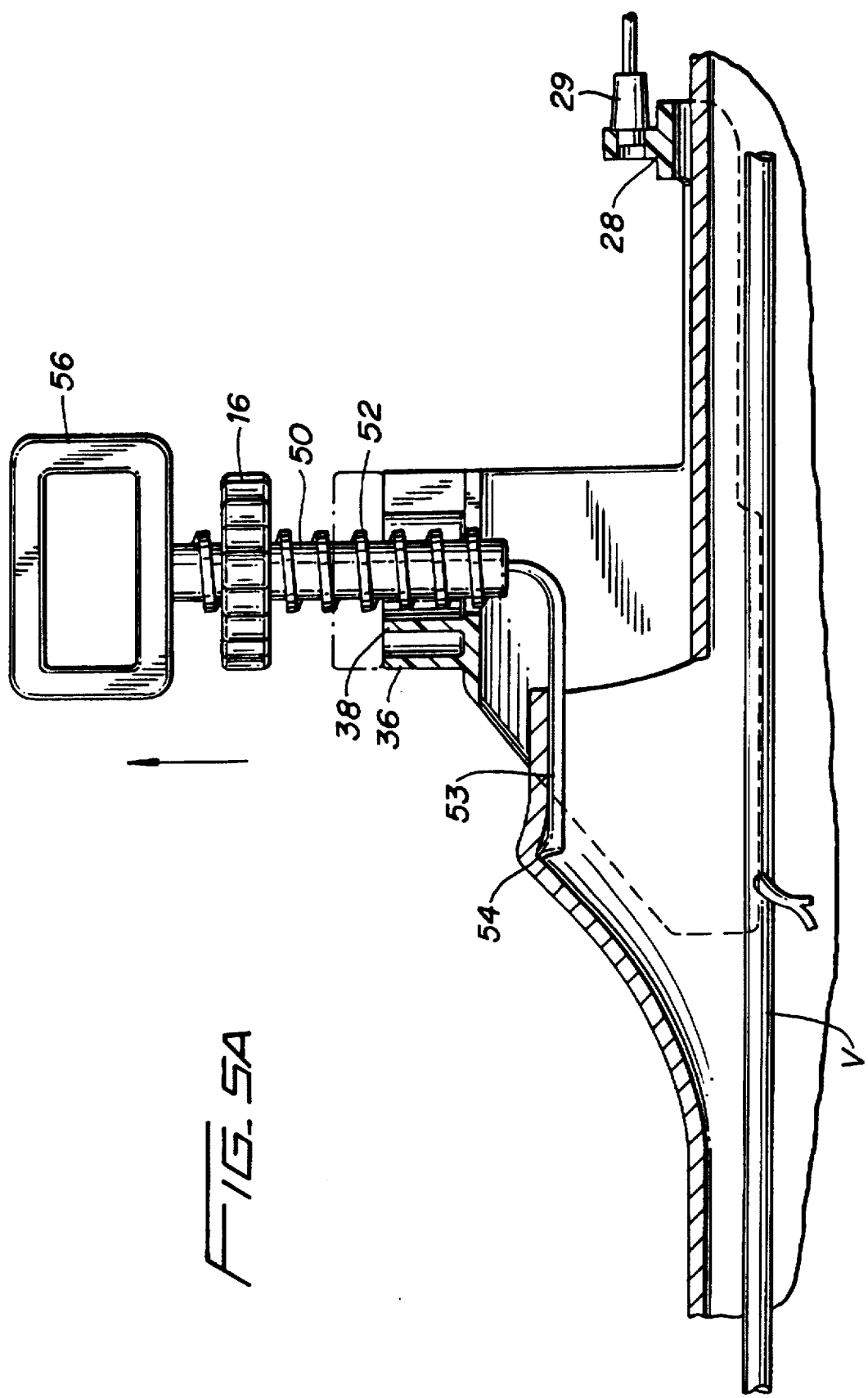

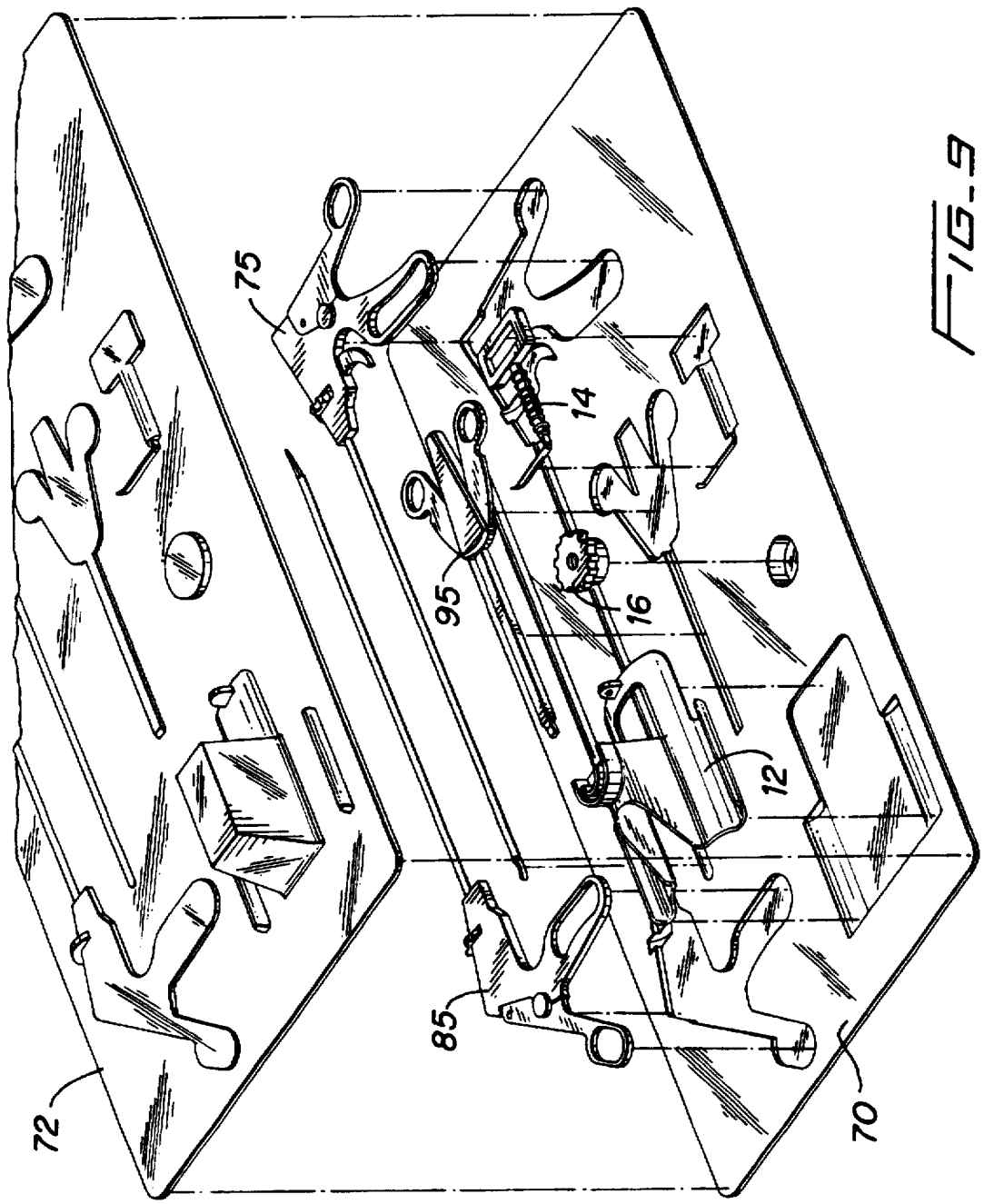

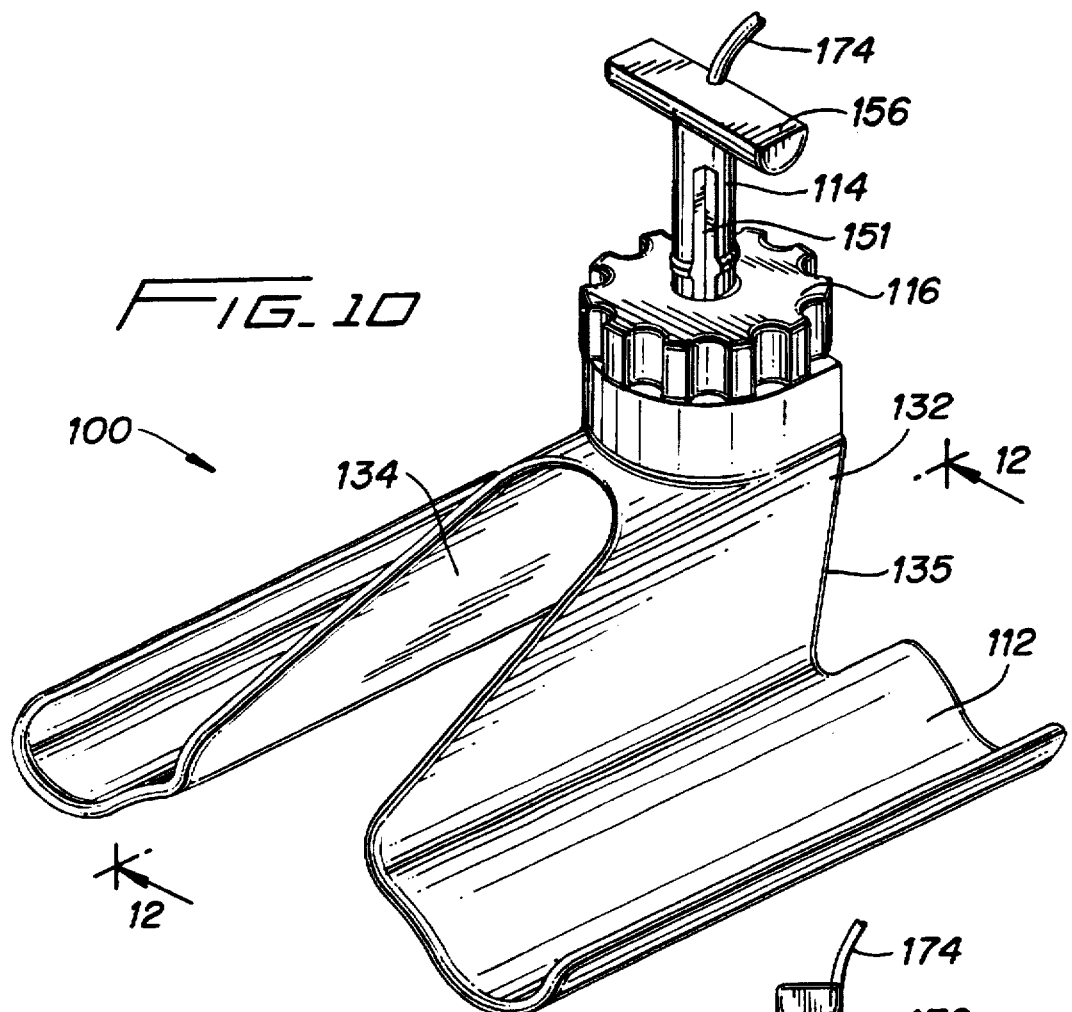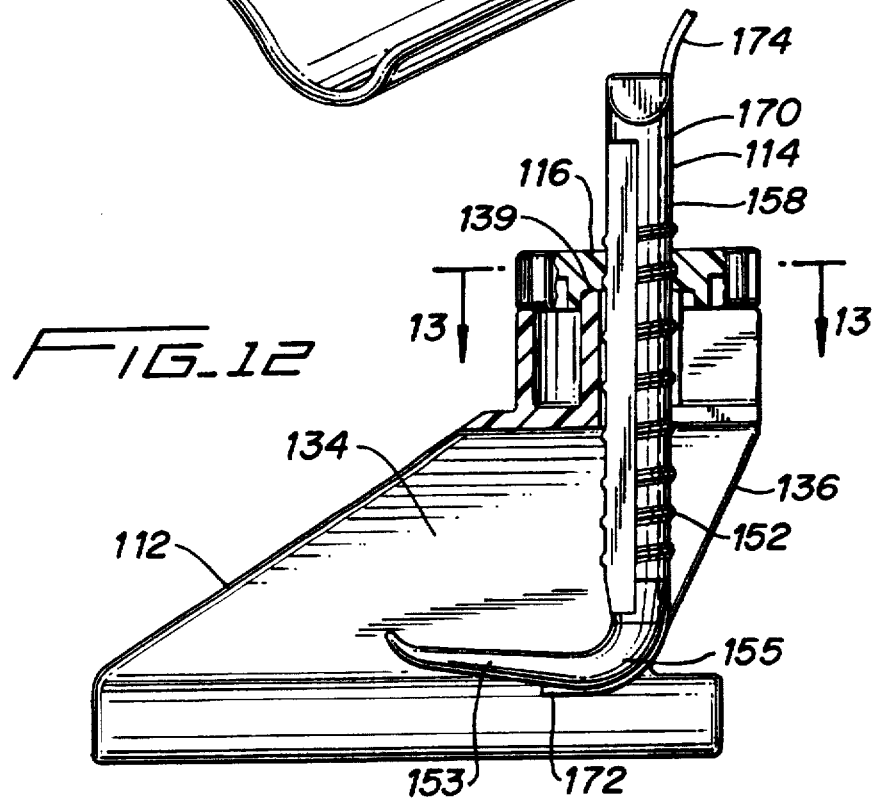

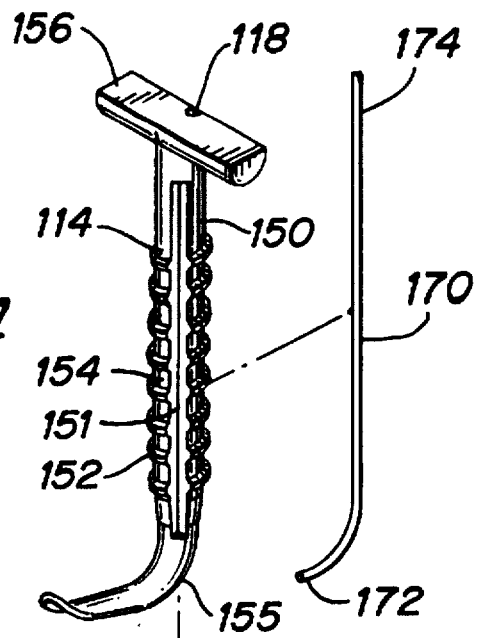
FIG_11
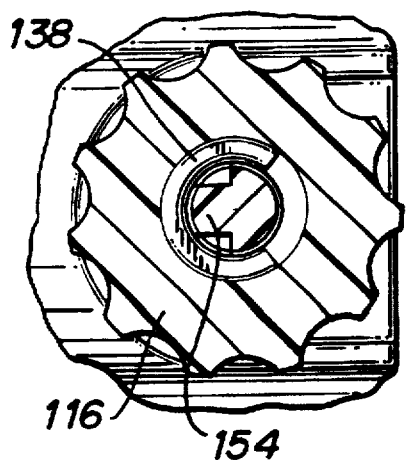
FIG_13
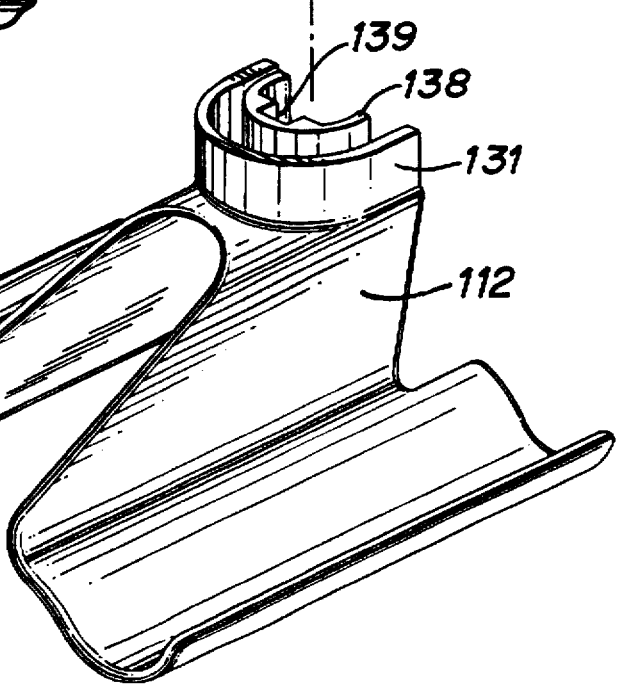

5,782,753

SURGICAL RETRACTOR

BACKGROUND

1. Technical Field

This application relates to a surgical retractor, and more particularly, to a surgical retractor which facilitates the harvesting of veins.

2. Background of the Related Art

In certain surgical procedures, it is necessary to remove an artery or vein from the patient. For example, in coronary artery bypass surgery (CABG), to re-route the blood flow to or from the heart to bypass a blockage in the coronary artery, an artery or vein is harvested from the patient and connected to the coronary artery to enable the unobstructed flow of blood.

In certain instances, e.g. when only a short graft is required, the mammary artery can be harvested and used for CABG. However, the mammary artery is oftentimes of insufficient length. Therefore, the patient's saphenous vein is most often utilized. The saphenous vein runs the length of the leg and is about ¼ to 1 inch below the skin. The most common method of removing the saphenous vein currently performed by surgeons involves making an incision in the patient's leg extending the length of the section of the vein to be removed. Frequently, this requires an incision running the entire length of the leg, from the ankle to the groin, which can be over 40 inches in length. Once the leg is opened in this manner, the surgeon, utilizing a light source supported on headgear or a headband, dissects the vein from the surrounding tissue and ligates and severs the vein from its numerous branches along its length. The vein is then cut at both ends and removed from the patient for use as a graft attached to the coronary artery or aorta. After removal of the vein, the leg incision is sutured.

Such formation of a large leg incision has many disadvantages. It is time consuming, complicates the procedure, creates a large scar, and increases the risk of infection and skin necrosis. It also adds to the expense of the procedure by requiring additional surgeon time to close the leg incision. Moreover, it increases the patient's discomfort and prolongs the patient's recovery time. In fact, the recovery time from the leg incision can take even longer than the recovery time from the chest incision from the heart surgery.

The need for a less invasive method and instrumentation to remove the saphenous vein is recognized in the field. For example, in U.K. Patent No. 2,082,459, an apparatus is disclosed for harvesting the saphenous vein utilizing two small incisions. A center rod is inserted into the lumen of the vein, and the tubular body having a series of cutting blades is introduced over the center rod and passed along the vein to cut the tributaries and fatty tissue around the vein. U.S. Pat. No. 4,793,346 to Mindlich discloses an apparatus which has a pair of knife blades extending from an elongate plastic tube. The tube has an inner diameter larger than the outer diameter of the vein. In use, the tube is inserted through an incision, and guided over the vein by a flexible guide which is inserted through the vein. The tube is rotated as it is advanced so that the knife blades can sever the vein branches. Electrically conductive wires are coupled to the knife blades to cauterize the severed end of the branches. U.S. Pat. No. 5,373,840 to Knighton discloses an endoscope and method for vein removal under visualization. A dissecting tool is inserted through one of the endoscope channels to separate the blood vessel from the connective tissue and a forceps is inserted through a second channel to hold the vessel during the procedure. The endoscope is inserted through a small incision and the dissecting tool is advanced along the vein. When a side branch is encountered, the dissection tool is removed and a ligating-cutting tool is inserted through the channel to sever the side branch.

Each of the instruments of the prior art described above are complex and expensive. Furthermore, they require the procedure to be performed in a tight working space as the vein is not separated from the surrounding tissue and the instruments are wedged between the vein and the tissue.

It would be advantageous to provide an apparatus which could minimally invasively separate the skin (and subcutaneous tissue) from the vein to enable dissecting and ligating instrumentation to be inserted through small incisions to facilitate removal of the saphenous vein. It would also be advantageous to equip such apparatus with illumination capabilities to enable the surgeon to better visualize the vein as it is dissected. This would not only eliminate the need for the surgeon to wear cumbersome head gear, but would avoid the expense involved with the use of an endoscope as well as avoid the additional time required for the constant withdrawal and reinsertion of the instruments through the endoscope's working channels.

SUMMARY

The present application discloses a retractor which advantageously increases the working space to facilitate minimally invasive harvesting of the vein from the patient. More specifically, the retractor lifts the skin and subcutaneous tissue away from the saphenous vein to improve visibility and enable dissecting and ligating instruments to more easily access the vein.

The retractor has a base adapted to lie on the patient's skin, a handle slidably mounted with respect to the base, a tissue retracting blade extending from the handle, and a locking member cooperating with the handle and movable to retain the tissue retracting blade in a selected position. The locking member preferably comprises a rotatable knob which engages threads on a shaft portion of the handle. The apparatus may include means for enabling illumination of the surgical site.

A method for accessing the saphenous vein to facilitate harvesting the vein is also disclosed comprising the steps of making a small incision in the leg of the patient, positioning a retractor on the patient's leg such that a retractor blade extends into the incision and a base portion lies on the surface of the patient's leg, and pulling the retractor blade away from the patient to lift the tissue away from the underlying saphenous vein.

BRIEF DESCRIPTION OF THE DRAWINGS

Various embodiments are described herein with reference to the drawings, wherein FIG. 1 is a perspective view of a first embodiment of the surgical retractor;

FIG. 2 is an exploded perspective view of the retractor of FIG. 1;

FIG. 3 is a cross-sectional view taken along lines 3—3 of FIG. 1 showing the handle and retractor blade in the initial position;

FIG. 4 is a perspective view showing the surgical retractor positioned in a first incision in the patient's left leg and the retractor handle in the initial position;

FIG. 5 is a perspective view similar to FIG. 4 showing the handle and retractor blade in the deployed position to separate the vein from the skin and subcutaneous tissue from the vein;

FIG. 5A is a cross-sectional view taken along lines 5A—5A of FIG. 5 showing the handle and retractor blade in the deployed position;

FIG. 6 is a perspective view similar to FIG. 5 showing rotation of the locking knob into the locking position to retain the handle and retractor blade in the selected position;

FIG. 9 is a perspective view of a surgical kit for harvesting the saphenous vein which includes the surgical retractor of FIG. 1;

FIG. 10 is a perspective view of an alternate embodiment of the surgical retractor;

FIG. 11 is an exploded perspective view of the retractor of FIG. 10;

FIG. 12 is a cross-sectional view of the surgical retractor taken along lines 12—12 of FIG. 10 showing the handle and retractor blade in the initial position; and FIG. 13 is a cross-sectional view taken along lines 13—13 of FIG. 12 showing the keyway for orienting the handle with respect to the base of the retractor.

DETAILED DESCRIPTION OF PREFERRED EMBODIMENTS

Figure 7:
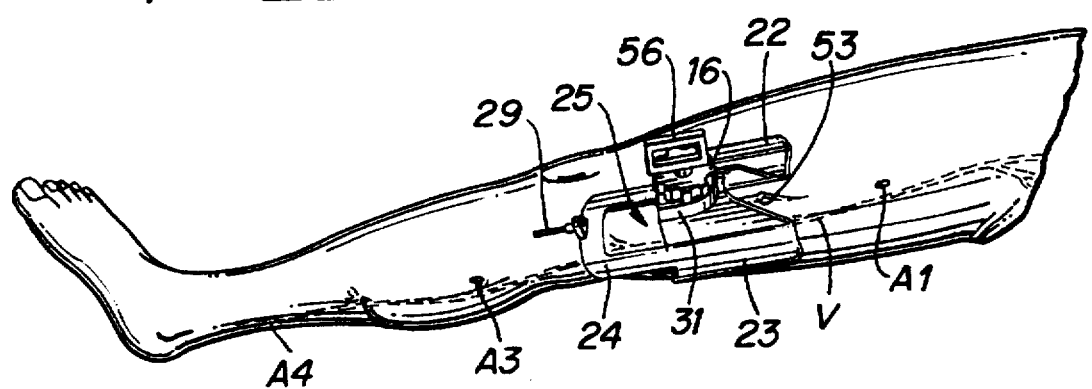
FIG. 7 is a perspective view illustrating the surgical retractor positioned in a second incision, oriented in the opposite direction of that of FIG. 4 and showing the handle and retractor blade in the initial position.

Referring now to the drawings wherein like reference numerals identify similar or identical parts throughout the views, and particularly to FIGS. 1–3, the surgical retractor of the present application is identified generally by reference numeral 10. Retractor 10 includes a handle 14 having a hook portion or retractor blade 53 for engaging the tissue to be retracted, a base 12 for supporting handle 14, and a locking knob 16 for retaining the handle 14 and retractor blade 53 in the selected position.

In short, the retractor blade 53 is placed inside a skin incision and is manually pulled upwardly by pulling on handle 14 to lift the tissue layers. This separates the lifted tissue from the underlying structure to improve access for performing the surgical procedure as described below.

Base 12 of retractor 10 has a pair of spaced apart legs 22, 23, extending from walls 32, 34, respectively, which curve upwardly and outwardly away from the center of the base 12. The skin engaging bottom surfaces 20, 21 of legs 22, 23, respectively, are adapted to lie on the patient's skin. Walls 32, 34 are spaced apart to form gap 25 to allow access to the surgical site with the necessary instrumentation.

Extension 24 has a support 28 with an aperture 27 formed therein configured to receive a conventional adapter 26 for mounting an optical fiber 29 to illuminate the surgical site. Alternatively, a light pipe can be provided to guide light from a conventional light source such as Storz Coldlight Fountain. Thus, the optical fiber or light pipe provides a means for enabling illumination of the surgical site as an alternative to the headgear currently worn by surgeons. It should be understood that the means for enabling illumination could alternately be positioned at other locations with respect to the base and the handle as long as it performs the desired function.

Walls 32, 34, as shown, extend downwardly and outwardly from neck portion 31 and are integrally formed with the respective leg 22, 23. A U-shaped outer wall 36 and a U-shaped inner wall 38 are formed on neck portion 31 and are configured to receive the locking knob 16 as best seen in FIG. 2. The opening in the U-shaped walls 36, 38 allows the handle 14 to be mounted to the base 12.

Handle 14 is slidably mounted with respect to base 12 and has a shaft 50 dimensioned for slidable reception in the opening in inner wall 38. Shaft 50 has an integral retractor blade 53 extending substantially perpendicular thereto, terminating in atraumatic tip 54. Although shown as integral, it is also contemplated that the retractor blade can be a separate element attached to shaft 50. A plurality of external threads 52 are formed along the length of shaft 50 to engage the internal threads on locking knob 16 as will be described below. Handle grip 56 is illustrated with an opening for the user's fingers to facilitate grasping. It should be appreciated that alternate grips can be utilized.

With continued reference to FIGS. 1–3, locking knob 16 has an axial opening 44 to receive shaft 50 of handle 14 and internal threads which engage the external threads 52 of handle 14. Cylindrical flange 42 is seated in the space between the inner and outer walls 38, 36 and bottom surface 43 rests on the upper surface of inner and outer walls 38, 36 when the locking knob 16 is in the locking position.

In use, retractor portion (blade) 53 is inserted through an incision formed in the patient and the base 12 is placed on the patient's skin. Handle grip 56 is grasped by the user and the handle 14 is pulled upwardly away from the patient. This causes the blade 53 to lift the patient's skin and a portion of the subcutaneous tissue. When the handle 14, i.e. the retractor blade 53, is in the desired position, locking knob 16 is rotated clockwise to slide it towards base 12 until flange 42 is seated in the space between the outer and inner walls 36, 38, and lower surface 43 rests on walls 36, 38, thereby locking handle 14 in position. This frees the surgeon's hands as it effectively retains the tissue in the lifted position without the surgeon having to hold the handle 14. When the surgeon desires to release the retractor blade 53, locking knob 16 is rotated counterclockwise, thereby releasing the locking engagement of locking knob 16 and shaft 50 to allow the handle 14 to be lowered to return the tissue to the initial portion. The retractor blade 53 can then be removed from the incision.

It should be noted that if controlled progressive lifting of the retractor blade 53 is desired, initially the locking knob 16 can be placed in the lowermost position, i.e. flange 42 positioned between U-shaped walls 36, 38 and lower surface 43 resting atop walls 38, 36. Rotation of knob 16 clockwise will then progressively move retractor blade 53 upwardly to lift the skin.

By way of example, the retractor of the present invention will be described in conjunction with saphenous vein harvesting as illustrated in FIGS. 4–8, although other uses of the retractor are possible. The retractor 10 advantageously enables the saphenous vein V to be harvested by requiring only several (e.g. four), small incisions in the leg, each about 40 mm. as contrasted with a longitudinal incision running the length of the leg. As shown, four incisions A1, A2, A3 and A4 are made in the leg, two above the knee and two below the knee. The retractor 10 is inserted into each incision to separate the surrounding tissue from the vein to improve access to the vein and increase the working space. More specifically, it lifts the tissue away from the vein to enable the vein to be dissected and ligated along the extent of its length which is accessible by the surgical instruments inserted through the incision. The retractor 10 is inserted in each incision in two directions (e.g. FIG. 4 and FIG. 7) so the vein can be accessed in both directions through each incision.

More particularly, as shown in FIG. 4, the retractor blade 53 of retractor 10 is placed through incision A1 in the leg with the engaging surfaces of legs 22, 23 of the base 12 resting on the patient's skin. Optical fiber 29 illuminates the surgical site. Handle grip 56 is pulled upwardly in the direction of the arrow of FIG. 5 to lift retractor blade 53, thereby lifting the skin and a portion of the subcutaneous tissue away from the saphenous vein V (see also FIG. 5A). When the skin and subcutaneous tissue have been lifted to a desired degree to provide a sufficient gap for visualization and access to the branches of the vein, locking knob 16 is rotated clockwise as shown in FIG. 6 to abut inner and outer walls 38, 36 to secure the handle shaft 50 in position. This locks the retractor blade 53 in position so the surgeon can release the handle 14 and free his hands for the procedure, with the blade 53 maintaining the working gap between the tissue and the vein.

If more controlled progressive lifting of the tissue is desired as described above, the locking knob 14 can initially be seated on the upper surface of inner and outer walls 38, 36 and rotated clockwise to progressively lift the retractor blade 53.

Once the tissue is lifted, a dissecting and ligating instrument are inserted through the gap 25 in the base 12 to legate and dissect the branches from the vein. As illustrated, this dissects and ligates the branches to the left of the incision as viewed in FIG. 4. On example of instruments which can be used are the Auto Suture ENDO SHEARS* instrument and Auto Suture PREMIUM SURGICLIP* clip applier (* denotes trademark of United States Surgical Corporation). A conventional retractor such as GELPI manufactured by George Tiemann Co., can be inserted through gap 25 to achieve lateral spreading of the tissue adjacent the vein. The light guide which is supported by support 28 illuminates the surgical site as the tissue is retracted as well as during dissection and litigation of the vein. After the branches of the vein are dissected within the reach of the instruments, the locking knob 16 is rotated counterclockwise to release the handle shaft 50 and allow the skin and subcutaneous tissue to return to its non-lifted (initial) position. The retractor 10 is then, in the same incision, reoriented 180° from the original position. The dissecting and ligating instruments can then be inserted again through gap 25 to separate the portion of the vein from the branches on the other side of the incision, i.e. to the right of the incision. As is apparent, this enables the portion of the vein to the right and the left of the incision to be dissected, limited by the reach of the instruments.

Figure 8:
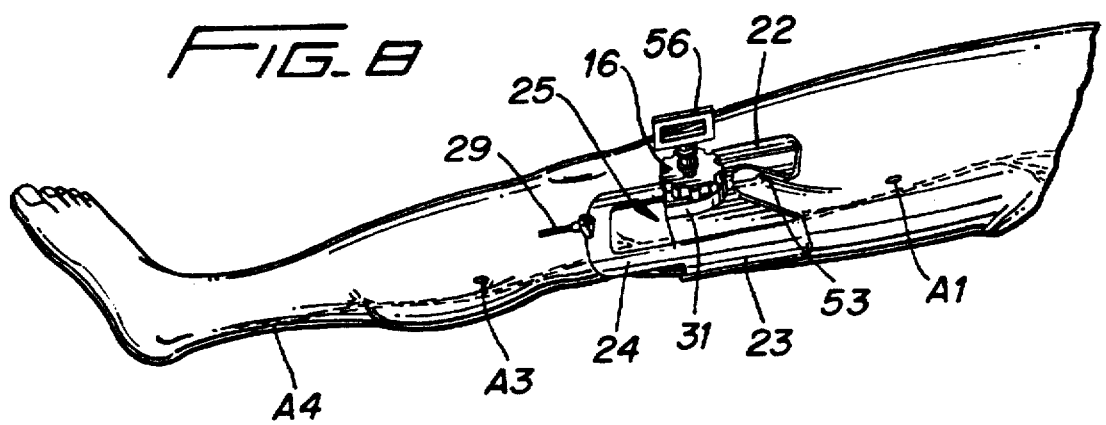
FIG. 8 is a perspective view similar to FIG. 7 illustrating the handle and retractor blade in the deployed position to separate the skin and subcutaneous tissue from the vein.

When the vein is severed in both directions through the first incision, the retractor 10 is then placed in the second incision A2. The skin and a portion of the subcutaneous tissue is lifted away from the vein as described above and the instruments are inserted to ligate and dissect the branches from the vein. Retractor 10 is then reoriented 180° in the incision A2 to ligate the portion of the vein extending in the other direction. FIG. 8 illustrates the retractor 10 positioned in the second incision oriented in the opposite direction from that shown in FIGS. 4–6. The retractor 10 is placed in each of the four incisions, oriented in both directions to access the vein in two directions. This enables access to the entire length of the vein through only four small incisions. Note that the extent the vein can be accessed in each direction through each incision is limited by the length of the ligating and dissecting instruments.

After all the branches are severed, the saphenous vein V is severed at both ends and removed from the leg through the incisions for use as a bypass graft. One way to remove the vein is to pull a portion of the vein up through incision A1, followed by pulling the vein portion around A1 through the incision A2, followed by A3 and finally through A4.

It should be appreciated that not only can more than four incisions be made, but fewer incisions can be utilized if a smaller section of the vein is desired or if longer instruments can be provided. Also, the order of insertion and orientation of the retractor 10 in each incision is not limited to the order discussed above.

The retractor 10 can be provided in a sterile package which includes the instrumentation for removing the vein from the leg. The kit, as shown by way of example in FIG. 9, includes a clip applier for ligating the branches of the vein, a dissector for severing the branches, and a grasper for holding the vein during dissection and ligation. An Auto Suture* ENDO GRASP, ENDO SHEARS, and PREMIUM SURGICLIP* instrument are shown, designated by reference numerals 75, 85 and 95, respectively. Clearly, other combinations of instruments can be included in the kit. As illustrated, recesses conforming to the shape of the instruments are formed in tray 70 with accompanying shaped recesses formed in cover 72.

Note that the retractor 10 can be packaged fully assembled or packaged with the three elements, i.e. the handle, base, and locking knob, separated for quick assembly by the user.

An alternate embodiment of the retractor is illustrated in FIGS. 10–13. Retractor 100 includes a base 112, a handle 114 and a locking knob 116. The base 112 functions in a similar manner as base 14, i.e., it rests on the patient's skin and mounts handle portion 114. However, as shown, it is different in configuration as, for example, extension 24 has been eliminated and walls 132 and 134 are angled at edges 135, 136 respectively.

The handle 114 has a hook portion or retractor blade 153 which progressively decreases in width towards the distal end to reduce the stress on the blade. A plurality of external threads 152 formed on shaft 150 engage the internal threads formed on locking knob 116. A pair of longitudinal grooves 151 (only one of which is shown) are formed along the length of the handle shaft 150 to create a projecting surface 154 which sits within the keyway (recess) 139 in the U-shaped inner wall 138 of neck portion 131 of base 112. This alignment of the projecting surface 154 and recess 139 ensure that the retractor blade 153 is oriented in the correct position during use and prevents rotation of handle portion 114.

On the portion of the handle shaft 150 opposite the projecting surface 154, (180° apart), is an elongated recess 158 configured to receive a light guide 170. As shown, the light guide 170 is in the form of a plastic tube which snaps into the elongated recess 158 and extends around the radiused portion 155 of retractor blade 153, terminating at distal tip 172 underneath retractor blade 153. The proximal end 174 of light guide 170 protrudes through opening 118 in handle grip 156 for connection to a conventional light source, such as Storz Coldlight Fountain. Thus, the light guide 170 provides means for enabling illumination for the surgical site. It should be appreciated that the means for enabling illumination can be positioned at other parts of the handle portion 114 or the base 112. For example, the tube 170 can be attached to the outside of the shaft 150. Also, although the means is disclosed as a light guide which cooperates with an independent light source, it is also contemplated that an illumination means which contains a light source can be included as part of the retractor.

The rotating knob 116 is similar to the rotating knob 16 of the first embodiment of FIGS. 1–3 except that instead of the flange 42, portion 139 of inner wall 138 extends upwardly to mount the locking knob 116. Locking knob 116 functions in an identical manner as locking knob 16 to retain the handle 114 and retractor blade 153 in the selected position.

The surgical retractor 100 is used in the identical fashion as retractor 10 described in FIGS. 4–8. The retractor 100 can also be packaged as a kit in the same manner as described above with respect to the first embodiment.

The retractor 10 or 100 can optionally be offered with retractor blades of different configurations. For example, the retractor can be packaged as a kit including two or more handles having retractor blades of different sizes.

It will be understood that various modifications may be made to the embodiments disclosed herein. For example, different shaped handles can be provided. Also the instrument can be entirely disposable or the entire instrument or parts thereof can be sterilized and reusable. Therefore, the above description should not be construed as limiting but as merely exemplifications of preferred embodiments. Those skilled in the art will envision other modifications within the scope and spirit of the claims appended thereto.

What is claimed is:

1. A surgical apparatus for retracting tissue comprising: a base adapted to lie on the patient's skin in a first plane, a handle positioned transverse to the first plane and slidably mounted with respect to the base, a tissue retracting blade extending from the handle and movable by movement of the handle, and a locking member cooperating with the handle and movable from at least a first position to a second position to retain the tissue retracting blade in a selected position.

2. A surgical apparatus according to claim 1 wherein the retracting blade extends transversely from the handle.

3. A surgical apparatus according to claim 2, wherein he handle includes a shaft, and the locking member comprises a rotatable knob mounted on the shaft of the handle.

4. A surgical apparatus according to claim 3, wherein the rotatable knob threadably engages threads on the shaft portion of the handle to retain the retracting blade in the selected position.

5. A surgical apparatus according to claim 1, further comprising a support for mounting a light guide to illuminate the surgical site.

6. The surgical apparatus according to claim 1, wherein the retracting blade is integral with the handle.

7. The surgical apparatus according to claim 1, wherein the base includes two spaced apart legs and the retracting blade is positioned between the legs.

8. The surgical apparatus according to claim 1, further comprising a light guide mounted on the handle.

9. The surgical apparatus according to claim 8, wherein the handle includes a shaft and the shaft includes a recess dimensioned and configured to receive the light guide.

10. A surgical apparatus comprising: a base adapted to lie on the patient's skin, a handle slidably mounted with respect to the base, a tissue retracting blade extending from the handle and movable by movement of the handle, and a locking member cooperating with the handle and movable from at least a first position to a second position to retain the tissue retracting blade in a selected position, wherein the base portion includes a pair of upstanding walls, each wall extending upwardly from the respective legs and terminating in a neck portion to support the locking member, and wherein the base includes two spaced apart legs and the retracting blade is positioned between the legs.

11. A surgical apparatus for retracting tissue comprising:
   a) a base having a neck portion and a pair of legs spaced apart to define a space therebetween, the legs configured for positioning on the patient's skin and the neck portion defining an opening;
   b) an elongated shaft positioned in the opening and the space and slidable with respect to the base;
   c) a retracting member extending from the shaft and configured for insertion into the patient's body; and
   d) a grip portion extending from the shaft for moving the retracting member away from the patient.

12. The apparatus of claim 11, further comprising a locking member for securing the retracting member in position with respect to the base.

13. The apparatus of claim 12, further comprising a light guide to illuminate the surgical site.

14. The apparatus of claim 13, wherein the locking member threadingly engages a portion of the shaft.

15. The apparatus of claim 11, wherein the retracting member is integral with the elongated shaft.

16. A surgical apparatus for retracting tissue comprising:
   a) a base having a pair of stationary legs spaced apart at a fixed distance;
   b) an elongated shaft movably mounted with respect to the base;
   c) a tissue retracting blade extending from the shaft and movable upon movement of the elongated shaft; and
   d) means mounted with respect to the base or the elongated shaft for enabling illumination of the surgical site.

17. The surgical apparatus according to claim 16, wherein the means for enabling illumination of the surgical site comprises a light guide mounted to the shaft portion.

18. The surgical apparatus according to claim 17, wherein the light guide is mounted within a recess in the shaft.

19. The surgical apparatus according to claim 16, further comprising a locking member, the locking member retaining the shaft in a desired position.

20. A method for accessing the saphenous vein to facilitate harvesting the vein comprising the steps of:
   a) making a small incision in the leg of a patient;
   b) positioning a retractor on the patient's leg such that a retractor blade extends into the incision and a base lies on the surface of the patient's leg;
   c) pulling the retractor blade away from the patient to lift the tissue away from the underlying saphenous vein.

21. The method of claim 20, wherein the step of pulling the retractor blade comprises the step of pulling a grip portion of a handle of the retractor.

22. The method of claim 21, further comprising the step of illuminating the saphenous vein during retraction.

23. The method of claim 20, further comprising the step of locking the retractor blade in the desired position.

24. The method of claim 20, wherein the step of locking the retractor blade comprises the step of rotating a locking knob into locking engagement with a shaft of the retractor.

* * * * *